United States Patent [19]

Levitt

[11] 4,221,585

[45] Sep. 9, 1980

[54] N-[(2,6-DIMETHOXYPYRIMIDIN-4-yl)-]AMINOCARBONYL BENZENE SULFONAMIDES AND THEIR HERBICIDAL COMPOSITIONS AND METHODS OF USE

[75] Inventor: George Levitt, Wilmington, Del.

[73] Assignee: E. I. Du Pont de Nemours and Company, Wilmington, Del.

[21] Appl. No.: 929,544

[22] Filed: Aug. 4, 1978

Related U.S. Application Data

[63] Continuation-in-part of Ser. No. 834,828, Sep. 19, 1977, abandoned.

[51] Int. Cl.$^3$ .................... A01N 43/48; C07D 239/69
[52] U.S. Cl. ............................................ 71/92; 71/90; 260/346.11; 260/347.2; 260/347.7; 544/310; 544/312; 544/327
[58] Field of Search ...................... 544/327, 310, 312; 71/92

[56] References Cited

U.S. PATENT DOCUMENTS 3,823,007  7/1974  Stephens et al. ...................... 71/103

FOREIGN PATENT DOCUMENTS 1468747  2/1967  France .

OTHER PUBLICATIONS

Wojciechowski, J. Acta Polon. Pharm., 19, pp. 121–125, (1962), [Chem. Ab., 59 1633e].
R. Morrison and N. Boyce, Organic Chemistry, 3rd Ed., Allyn and Bacon Inc., Boston, (1974), p. 1044.

*Primary Examiner*—Donald G. Daus
*Assistant Examiner*—Lisa Jones

[57] ABSTRACT

N-(heterocyclicaminocarbonyl)sulfonamides, such as N-[(2,6-dimethoxypyrimidin-4-yl)aminocarbonyl]-2-methylbenzenesulfonamide are useful for the regulation of plant growth and as preemergence and postemergence herbicides.

36 Claims, No Drawings

N-[2,6-DIMETHOXYPYRIMIDIN-4yl)] AMINOCARBONYL BENZENE SULFONAMIDES AND THEIR HERBICIDAL COMPOSITIONS AND METHODS OF USE

RELATED APPLICATIONS

This application is a continuation-in-part of my copending application U.S. Ser. No. 834,828 filed Sept. 19, 1977, now abandoned.

BACKGROUND OF THE INVENTION

This invention relates to N-(heterocyclicaminocarbonyl)sulfonamide agricultural chemical compounds, formulations containing the same and methods of using such compounds.

Wojciechowski, J. Acta. Polon. Pharm. 19, p. 121-5 (1962) [Chem. Ab., 59 1633 e] describes the synthesis of N-[(2,6-dimethoxypyrimidin-4-yl)aminocarbonyl]-4-methylbenzenesulfonamide:

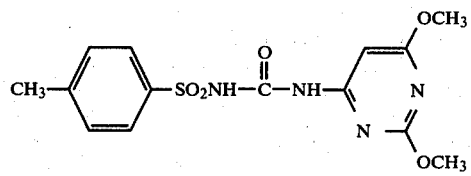

Based upon similarity to a known compound, the author predicted hypoglycemic activity for the foregoing compound.

U.S. Pat. No. 3,637,366 discloses compounds having the formula:

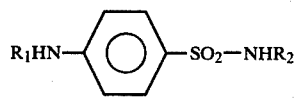

wherein $R_1$ is hydrogen or lower saturated aliphatic acyl and
$R_2$ is hydrogen, 2-pyrimidinyl, pyridyl, amidino, acetyl or carbamoyl.

The disclosed compounds are said to provide control of crabgrass, cress, endive, clover and *Poa annua*.

French Pat. No. 1,468,747 discloses the following para-substituted phenylsulfonamides, useful as antidiabetic agents:

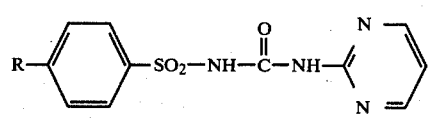

wherein R=H, halogen, $CF_3$ or alkyl.

Logemann et al., Chem. Ab. 53, 18052 g (1959), disclose a number of sulfonamides, including uracil derivatives and those having the formula:

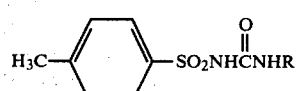

wherein R is butyl, phenyl or

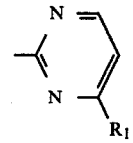

and $R_1$ is hydrogen or methyl. When tested for hypoglycemic effect in rats (oral doses of 25 mg/100 g), the compounds in which R is butyl and phenyl were most potent. The others were of low potency or inactive.

The presence of undesired vegetation causes substantial damage to useful crops, especially agricultural products that satisfy man's basic food and fiber needs, such as cotton, rice, corn, wheat and the like. The current population explosion and concomitant world food and fiber shortage demand improvements in the efficiency of producing these crops. Preventing or minimizing loss of a portion of such valuable crops by killing or inhibiting the growth of, undesired vegetation is one way of improving this efficiency.

A wide variety of materials useful for killing or inhibiting (controlling) the growth of undesired vegetation is available; such materials are commonly referred to as herbicides. However, the need still exists for effective herbicides that destroy or control weeds while not significantly damaging useful crops. Some weeds (nutsedge is a particular example) are very difficult to control; many of the herbicides that are used to control nutsedge are so nonselective that they cause damage to the crops themselves.

SUMMARY OF THE INVENTION

According to this invention, there are provided novel compounds of Formula I and their agriculturally suitable salts, suitable agricultural compositions containing them and methods of using them as general herbicides having both preemergence and postemergence activity

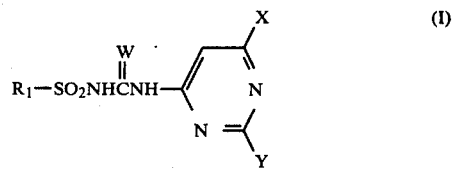

wherein
$R_1$ is

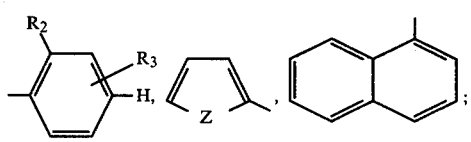

$R_2$ and $R_3$ are independently hydrogen, nitro, trifluoromethyl, fluorine, chlorine, bromine, methyl or methoxy;

W and Z are independently oxygen and sulfur; and
X and Y are independently hydrogen, chlorine, bromine, methyl, methoxy, or ethoxy;
and their agriculturally suitable salts; provided that at least one of X or Y must be other than hydrogen.

Preferred for their higher activity or favorable cost or both are those compounds of Formula I wherein (a) $R_1$ is

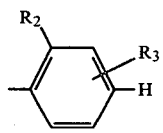

and, independently, (b) $R_2$ is chlorine, trifluoromethyl, nitro or methyl; or
(c) $R_3$ is hydrogen; or
(d) X and Y are both methoxy.

More preferred for their higher activity or more favorable cost or both, among the preferred compounds, are those compounds of Formula I wherein $R_2$ is chlorine, nitro or methyl, $R_3$ is hydrogen; and X and Y are both methoxy.

Most preferred for their excellent activity or more favorable cost or both, among the preferred compounds, are those compounds of Formula I wherein $R_2$ is chlorine, nitro or methyl; $R_3$ is hydrogen; X and Y are both methoxy; and W is oxygen.

Specifically preferred for their outstanding activity or highly favorable cost or both are:

(1) N-[(2,6-dimethoxypyrimidin-4-yl)aminocarbonyl]-2-methylbenzenesulfonamide;
(2) N-[(2,6-dimethoxypyrimidin-4-yl)aminocarbonyl]-2-chlorobenzenesulfonamide;
(3) N-[(2,6-dimethoxypyrimidin-4-yl)aminocarbonyl]-2-nitrobenzenesulfonamide;
(4) N-[(2-methoxy-6-chloropyrimidin-4-yl)aminocarbonyl]-2-nitrobenzenesulfonamide;
(5) N-[(2,6-dichloropyrimidin-4-yl)aminocarbonyl]-2-nitrobenzenesulfonamide.

Synthesis

As shown in equation 1, the compounds of Formula I can be prepared by reacting an appropriate 4-amino pyrimidine of Formula III with an appropriately substituted sulfonyl isocyanate or isothiocyanate of Formula II; $R_1$, W, X and Y being as previously defined.

Equation 1.

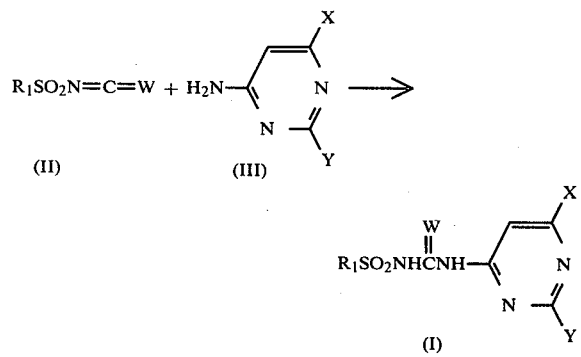

The reaction is best carried out in inert aprotic organic solvents such as methylene chloride, tetrahydrofuran or acetonitrile, at ambient pressure and temperature. The mode of addition is not critical; however, it is often convenient to add the sulfonyl isocyanate or isothiocyanate to a stirred solution of the aminopyrimidine. Since such isocyanates or isothiocyanates usually are liquids, their addition can be easily controlled.

The reaction is generally exothermic. In some cases, the desired product is insoluble in the warm reaction medium and crystallizes from it in pure form. Products soluble in the reaction medium are isolated by evaporation of the solvent, trituration of the solid residue with solvents such as 1-chlorobutane or ethyl ether, and filtration.

The intermediate sulfonyl isocyanates of Formula II (wherein W is O) can be prepared by reacting corresponding sulfonamides with phosgene in the presence of n-butyl isocyanate at reflux in a solvent such as chlorobenzene, according to the procedure of H. Ulrich and A. A. Y. Sayigh, *Newer Methods of Preparative Organic Chemistry*, Vol. VI, p. 223-241, Academic Press, New York and London, W. Foerst, Ed.

The preparation of sulfonamides from ammonium hydroxide and sulfonyl chlorides is widely reported in the literature, e.g. Crossley et al., *J. Am. Chem. Soc.* 60, 2223 (1938). The preparation of 2-furansulfonamide is described in *J. Org. Chem.* 18 894 (1953).

Certain sulfonyl chlorides are best prepared by chlorosulfonation of a substituted benzene, naphthalene, or thiophene in carbon tetrachloride according to the teaching of H. T. Clarke et al., *Org. Synth.* Coll. Vol. 1, 2nd Ed. 1941, p. 85. Other benzenesulfonyl chlorides are best made by diazotization of the appropriate aniline with sodium nitrite in HCl, followed by reaction of the diazonium salt with sulfur dioxide and cuprous chloride in acetic acid according to the teaching of H. L. Yale and F. Sowinski, *J. Org. Chem.* 25 1824 (1960).

Furansulfonylchlorides are best prepared as shown in Equation 2.

Equation 2.

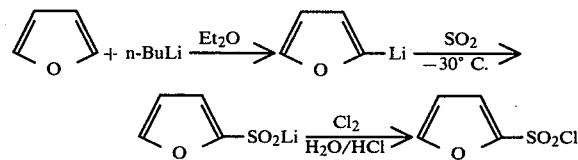

Sulfonyl isothiocyanates can be prepared by treatment of sulfonamides with carbon disulfide and potassium hydroxude followed by reaction of the dipotassium salt with phosgene according to the teaching of K. Hartke, *Arch. Pharm.*, 299, 174 (1966).

The synthesis of heterocyclic amine derivatives has been reviewed in "The Chemistry of Heterocyclic Compounds", a series published by Interscience Publ., New York and London. 4-Aminopyrimidines are described by D. J. Brown in "The Pyrimidines", Vol. XVI of the above series.

Agriculturally suitable salts of compounds of Formula I are also useful herbicides and can be prepared by a number of ways known to the art. For example, metal salts can be made by treating compounds of Formula I with a solution of alkali or alkaline earth metal salt having a sufficiently basic anion (e.g. hydroxide, alkoxide, carbonate or hydride). Quaternary amine salts can be made by similar techniques.

Salts of compounds of Formula I can also be prepared by exchange of one cation to another. Cationic exchange can be effected by direct treatment of an aqueous solution of a salt of a compound of Formula I (e.g. alkali metal or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g. an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water soluble.

Acid addition salts, useful in this invention, can be obtained by reacting a compound of Formula I with a suitable acid, e.g. p-toluenesulfonic acid, trichloroacetic acid or the like.

The compounds of this invention and their preparation are further illustrated by the following examples wherein temperatures are given in degrees centigrade.

EXAMPLE 1

N-[(2,6-dimethoxypyrimidin-4-yl)aminocarbonyl]-2-methylbenzenesulfonamide

To a stirred mixture of 2.40 g of 4-amino-2,6-dimethoxypyrimidine in 40 ml methylene chloride at ambient temperature and pressure was slowly added 3.0 g of 2-methylbenzenesulfonylisocyanate. The reaction was stirred 40 minutes, filtered, and the solid thereby obtained was washed with a small amount of acetonitrile; yield 4.0 g, m.p. 174°-175°, NMR (DMSO-d$_6$) relative to tetramethylsilane: δ 2.77, S, area 30; δ 4.05, S, area 60; δ 6.85, S, area 89; δ 7.7-8.6, multiplets, area 45; δ 10.00, S, area 9.

EXAMPLE 2

N-[(2,6-dimethoxypyrimidin-4-yl)aminocarbonyl]-2-chlorobenzenesulfonamide

To a mixture of 1.10 g of 4-amino-2,6-dimethoxypyrimidin in 40 ml methylene chloride at ambient temperature and pressure was added 1.60 g of 2-chlorobenzenesulfonylisocyanate. The reaction was stirred 30 minutes and then refluxed an additional 15 minutes. Volatiles were removed under reduced pressure and the solid thereby obtained was washed with a little diethyl ether; yield 2.30 g, m.p. 193°-196°.

EXAMPLE 3

2-Furansulfonylisocyanate

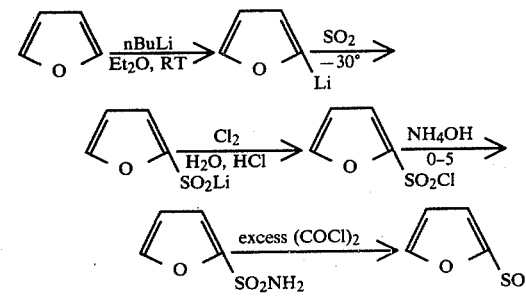

A. Lithium-2-furansulfinate

To a solution of 39.6 g of furan (585 mm) in 200 ml anhydrous ethyl ether was added carefully, under nitrogen atmosphere, 400 ml of 1.6 M n-butyl lithium in hexane while maintaining the reaction temperature at 30° or lower. The mixture was stirred until precipitation appeared complete. After cooling to −25° to −30°, excess gaseous sulfur dioxide was slowly passed through the mixture during a 2-hour period. The mixture was stirred at room temperature for an additional 90 minutes and the precipitated lithium-2-furansulfinate was filtered and washed with acetone. m.p. 250°. IR (Nujol) 3400-3000 cm$^{-1}$ (W), 1700 cm$^{-1}$, 1500 cm$^{-1}$ (VW), 1210 cm$^{-1}$, 1140 cm$^{-1}$, 1115 cm$^{-1}$ (m), 1020 cm$^{-1}$ (VS), 910 cm$^{-1}$, 880 cm$^{-1}$, 825 cm$^{-1}$ (W), 735 cm$^{-1}$ (S).

B. 2-Furansulfonyl chloride

Ninety ml of water, 410 ml of conc. HCl, and 68.0 g of lithium 2-furansulfinate were stirred and cooled to 10°-15°. Liquid chlorine (12.3 ml, 39.4 g) was added dropwise over a 30-minute period. The mixture was stirred an additional 30 minutes at 5°, poured onto ice and extracted with methylene chloride. Evaporation of the methylene chloride yielded 44 g of 2-furansulfonyl chloride, b.p. 95° at 7 mm Hg; IR (neat) 3400 (m), 3120, 1800, 1550 (m), 1450 (S), 1380 (VS), 1210, 1160, 1120 (VS), 1035 (m), 1010 (VS), 913, 882 (S).

C. 2-Furansulfonamide

Twenty-three g of 2-furansulfonyl chloride (138 mm) was added dropwise into 200 ml of conc. NH$_4$OH at 0°-5°. After stirring overnight at room temperature, the water was removed under vacuum and the precipitate washed with ice water and dried. Yield: 14 g of 2-furansulfonamide, m.p. 120°-122° (literature m.p. 120°-122°: JOC 18, 894 (1953)). IR (Nujol) 3250 cm$^{-1}$, 3100 cm$^{-1}$, 1600 cm$^{-1}$ (W), 1550 cm$^{-1}$, 1310 cm$^{-1}$, 1190 cm$^{-1}$, 1140 cm$^{-1}$, 1120 cm$^{-1}$, 1055 cm$^{-1}$, 1005 cm$^{-1}$, 930 cm$^{-1}$, 880 cm$^{-1}$, 843 cm$^{-1}$ (S).

D. 2-Furansulfonyl isocyanate

Dry toluene (150 ml), 25 ml of oxalyl chloride (295), and a trace of DABCO (diaza-bicyclo[2.2.2]octane) were heated to 90°. Ten g of 2-furansulfonamide was added over a 15 minute period and the mixture was held at 95° for 2 hours. After filtering, the solvent was removed under vacuum to yield 2.1 g of an oil showing the characteristic isocyanate absorption in the infrared (2280 cm$^{-1}$).

By using an equivalent amount of an appropriate 4-aminopyridmine and an appropriately substituted sulfonyl isocyanate or sulfonylisothiocyanate, the following compounds of Formula I can be prepared by the procedures of Examples 1 or 2.

TABLE 1

| W | R$_2$ | R$_3$ | m.p. °C. |
|---|---|---|---|
| O | H | H | 198-201 |
| O | F | H | |
| O | F | 3-Cl | |
| O | F | 5-F | |
| O | OCH$_3$ | 5-OCH$_3$ | |
| O | Cl | 5-OCH$_3$ | |
| O | Cl | 5-Cl | |
| O | CH$_3$ | 5-Cl | |
| O | Cl | 5-CH$_3$ | |
| O | CH$_3$ | 5-CH$_3$ | |
| O | Cl | 5-CH$_3$ | |
| O | Br | 5-Br | |
| O | Cl | 3-Cl | |
| O | OCH$_3$ | 5-Cl | |

TABLE 1-continued

[Structure: benzene ring with H, R₃, R₂ substituents, SO₂NHCNH-W double bond, connected to pyrimidine ring with OCH₃ groups at 2,6-positions]

| W | R₂ | R₃ | m.p. °C. |
|---|----|----|----------|
| O | Cl | 6-Cl | |
| O | NO₂ | H | 166–173 |

TABLE 2

[Structure: benzene ring with SO₂NHCNH-W, connected to pyrimidine with CH₃ and OCH₃ substituents]

| W | R₂ | R₃ | m.p. °C. |
|---|----|----|----------|
| O | H | H | |
| O | Br | H | |
| O | F | H | |
| O | CH₃ | H | 168–170 |
| O | Cl | H | |
| O | Cl | 3-CH₃ | |
| O | OCH₃ | 5-Cl | |
| O | CH₃ | 5-F | |
| O | Cl | 5-Cl | |
| O | F | 5-Cl | |
| O | CH₃O | 5-CH₃O | |
| O | F | 6-F | |
| O | Cl | 6-Cl | |
| O | Cl | 6-CH₃ | |

TABLE 3

[Structure: benzene ring with SO₂NHCNH-W, connected to pyrimidine with OCH₃ and CH₃ substituents]

| W | R₂ | R₃ | m.p. °C. |
|---|----|----|----------|
| O | Cl | H | 211–214 |
| O | CH₃ | H | 195–200(d) |

TABLE 4

[Structure: benzene ring with SO₂NHCNH-W, connected to pyrimidine with two CH₃ substituents]

| W | R₂ | R₃ | m.p. °C. |
|---|----|----|----------|
| O | H | H | 195–202 |
| O | Cl | H | 142–144 |
| O | CH₃ | H | |
| O | H | 3-Cl | |
| O | Cl | 3-Cl | |
| O | OCH₃ | 3-Cl | |
| O | CH₃ | 3-Cl | |

TABLE 4-continued

| W | R₂ | R₃ | m.p. °C. |
|---|----|----|----------|
| O | CH₃ | 5-F | |
| O | Br | 5-Br | |
| O | CH₃ | 5-Br | |
| O | Cl | 6-Cl | |
| O | F | 6-F | |
| S | H | H | |
| S | CH₃ | H | |
| S | Cl | H | |
| S | F | H | |
| S | OCH₃ | 5-Cl | |
| S | CH₃ | 5-CH₃ | |
| S | CH₃ | 5-Cl | |
| O | NO₂ | H | 211–213 |

TABLE 5

[Structure: benzene ring with SO₂NHCNH-W, connected to pyrimidine with X and Y substituents]

| W | R₂ | R₃ | X | Y | m.p. °C. |
|---|----|----|---|---|----------|
| O | Cl | H | OCH₃ | H | |
| O | Cl | H | H | OCH₃ | |
| O | CH₃ | H | CH₃ | H | |
| O | CH₃ | H | H | CH₃ | |
| O | NO₂ | H | Cl | OCH₃ | 167–188 |
| O | NO₂ | H | Cl | Cl | 130–144 |
| O | NO₂ | H | Br | Br | |
| O | NO₂ | H | OC₂H₅ | OC₂H₅ | |
| O | Cl | H | Cl | OC₂H₅ | |

TABLE 6

[Structure: R₁-SO₂NHCNH-W connected to pyrimidine with X and Y substituents]

| W | R | X | Y | m.p. °C. |
|---|---|---|---|----------|
| O | 2-thienyl | OCH₃ | OCH₃ | 203–206 |
| O | 2-furyl | CH₃ | OCH₃ | |
| O | 1-naphthyl | CH₃ | CH₃ | |
| S | 2-thienyl | CH₃ | CH₃ | |
| S | 1-naphthyl | CH₃ | CH₃ | |

EXAMPLE 4

N-[(2,6-dimethoxypyrimidin-4-yl)aminocarbonyl]-2-methylbenzenesulfonamide, sodium salt A mixture prepared from 500 ml of water, 4 g of sodium hydroxide and 35.3 g of N-[(2,6-dimethoxypyrimidin-4-yl)aminocarbonyl]-2-methylbenzenesulfonamide, prepared in Example 1 is stirred until the sulfonamide is dissolved. The solution which contains the desired sodium salt may be used for the purpose of this invention. If desired, the water is removed by evaporation in-vacuo and the isolated salt is washed with ethyl ether and dried.

By using equivalent amounts of the appropriate compound of Formula I and the appropriate base, the following salts of Formula I can be prepared.

| Base | $R_2$ | $R_3$ | W | X | Y | Cation |
|------|-------|-------|---|---|---|--------|
| NaOH | Cl | H | O | $OCH_3$ | $OCH_3$ | $Na^+$ |
| KOH | $NO_2$ | H | O | $OCH_3$ | $OCH_3$ | $K^+$ |
| ⌬—$CH_2N(CH_3)_3OH$ | H | H | O | $OCH_3$ | $OCH_3$ | ⌬—$CH_2\overset{+}{N}(CH_3)_3$ |
| $C_{12}H_{25}N(CH_3)_3OH$ | $CH_3$ | H | S | $OCH_3$ | $CH_3$ | $C_{12}H_{15}N^+(CH_3)_3$ |
| LiOH | Cl | 5-Cl | O | $OCH_3$ | $OCH_3$ | $Li^+$ |
| $(CH_3)_4NOH$ | F | H | O | $OCH_3$ | $OCH_3$ | $(CH_3)_4N^+$ |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. Generally, the formulations contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE 7

|  | Active Ingredient | Diluent(s) | Surfactant(s) |
|--|-------------------|------------|---------------|
| Wettable Powders | 20–90 | 0–74 | 1–10 |
| Oil Suspensions, Emulsions, Solutions (including Emulsifiable Concentrates) | 3–50 | 40–95 | 0–15 |
| Aqueous Suspensions | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins et al., "Handbook of Insecticide Dust Diluents and Carriers", 2nd Ed., Dorland Books, Caldwell, New Jersey. The more absorptive diluents are preferred for wettable powders and the denser ones for dusts. Typical liquid diluents and solvents are described in Marsden, "Solvents Guide", 2nd Ed., Interscience, New York (1950). Solubility under 0.1% is preferred for suspension concentrates; solution concentrates are preferably stable against phase separation at 0° C. "McCutcheon's Detergents and Emulsifiers Annual", MC Publishing Corp., Ridgewood, New Jersey, as well as Sisely and Wood, "Encyclopedia of Surface Active Agents", Chemical Publishing Co., Inc., New York (1964), list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 4th Ed., McGraw-Hill, New York (1963), pp. 8-59 ff.

For further information regarding the art of formulation, see for example:

H. M. Loux, U.S. Pat. No. 3,235,361, Feb. 15, 1966, Col. 6, line 16 through Col. 7, line 19 and Examples 10 through 41.

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167, 169–182.

H. Gysin and E. Knusli, U.S. Pat. No. 2,891,855, June 23, 1959, Col. 3, line 66 through Col. 5, line 17 and Examples 1–4.

G. C. Klingman, "Weed Control as a Science", John Wiley & Sons, Inc., New York (1961), pp. 81–96.

J. D. Fryer and S. A. Evans, "Weed Control Handbook", 5th Ed., Blackwell Scientific Publications, Oxford, (1968), pp. 101–103.

The compounds of Formula I can be formulated using the procedures of Examples 4–18. In the following examples, all parts are by weight unless otherwise indicated.

EXAMPLE 5

| Wettable Powder | |
|---|---|
| N-[(2,6-dimethoxypyrimidin-4-yl)-aminocarbonyl]-2-methylbenzenesul- | 80% |

-continued

| Wettable Powder | |
|---|---|
| fonamide | |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns and then reblended.

EXAMPLE 6

| Wettable Powder | |
|---|---|
| N-[(2,6-dimethoxypyrimidin-4-yl)-aminocarbonyl]benzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles of active essentially all below 10 microns in diameter. The product is reblended before packaging.

EXAMPLE 7

| Granule | |
|---|---|
| wettable powder of Example 5 | 5% |
| attapulgite granules (U.S.S. 20–40 mesh; 0.84–0.42 mm) | 95% |

A slurry of wettable powder containing ≃25% solids is sprayed on the surface of attapulgite granules in a double-cone blender. The granules are dried and packaged.

EXAMPLE 8

| Extruded Pellet | |
|---|---|
| N-[(2,6-dimethoxypyrimidin-4-yl)amino-carbonyl]-2-methylbenzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass on a U.S.S. No. 20 sieve (0.84 mm openings). The granules held on a U.S.S. No. 40 sieve (0.42 mm openings) may be packaged for use and the fines recycled.

EXAMPLE 9

| Oil Suspension | |
|---|---|
| N-[(2,6-dimethoxypyrimidin-4-yl)amino-carbonyl]-2-methylbenzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 10

| Wettable Powder | |
|---|---|
| N-[(2,6-dimethoxypyrimidin-4-yl)amino-carbonyl]-2-methylbenzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer mill to produce particles essentially all below 100 microns, the material is reblended and sifted through a U.S.S. No. 50 sieve (0.3 mm openings) and packaged.

EXAMPLE 11

| Low Strength Granule | |
|---|---|
| N-[(2,6-dimethoxypyrimidin-4-yl)amino-carbonyl]benzenesulfonamide | 1% |
| N,N-dimethylformamide | 9% |
| attapulgite granules (U.S.S. 20–40 mesh) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 12

| Aqueous Suspension | |
|---|---|
| N-[(2,6-dimethoxypyrimidin-4-yl)amino-carbonyl]benzenesulfonamide | 40% |
| polyacrylic acid thickener | 0.3% |
| dodecylphenol polyoxyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 13

| Solution | |
|---|---|
| N-[(2,6-dimethoxypyrimidin-4-yl)amino-carbonyl]benzenesulfonamide | 5% |
| water | 95% |

The compound is added directly to the water with stirring to produce solution, which may then be packaged for use.

EXAMPLE 14

| Low Strength Granule | |
|---|---|
| N-[(2,6-dimethoxypyrimidin-4-yl)amino-carbonyl]-2-methylbenzenesulfonamide | 0.1% |

-continued

| Low Strength Granule | |
|---|---|
| attapulgite granules (U.S.S. 20–40 mesh) | 99.9% |

The active ingredient is dissolved in a solvent and the solution is sprayed upon dedusted granules in a double cone blender. After spraying of the solution has been completed, the material is warmed to evaporate the solvent. The material is allowed to cool and then packaged.

EXAMPLE 15

| Granule | |
|---|---|
| N-[(2,6-dimethoxypyrimidin-4-yl)amino-carbonyl]benzenesulfonamide | 80% |
| wetting agent | 1% |
| crude ligninsulfonate (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and then packaged for use.

EXAMPLE 16

| High Strength Concentrate | |
|---|---|
| N-[(2,6-dimethoxypyrimidin-4-yl)amino-carbonyl]-2-methylbenzenesulfonamide | 99.0% |
| silica aerogel | 0.5% |
| synthetic amorphous silica | 0.5% |

The ingredients are blended and ground in a hammer mill to produce a material essentially all passing a U.S.S. No. 50 screen (0.3 mm opening). The concentrate may be formulated further if necessary.

EXAMPLE 17

| Wettable Powder | |
|---|---|
| N-[(2,6-dimethoxypyrimidin-4-yl)amino-carbonyl]benzenesulfonamide | 95.0% |
| dioctyl sodium sulfosuccinate | 0.1% |
| synthetic fine silica | 4.9% |

The ingredients are blended and ground in a hammer mill to produce particles essentially all below 100 microns. The material is sifted through a U.S.S. No. 50 screen and then packaged.

EXAMPLE 18

| Wettable Powder | |
|---|---|
| N-[(2,6-dimethoxypyrimidin-4-yl)amino-carbonyl]-2-methylbenzenesulfonamide | 40% |
| sodium ligninsulfonate | 20% |

-continued

| Wettable Powder | |
|---|---|
| montmorillonite clay | |

The ingredients are thoroughly blended, coarsely hammer-milled and then air-milled to produce particles essentially all below 10 microns in size. The material is then reblended and packaged.

EXAMPLE 19

| Oil Suspension | |
|---|---|
| N-[(2,6-dimethoxypyrimidin-4-yl)amino-carbonyl]benzenesulfonamide | 35% |
| blend of polyalcohol carboxylic esters and oil soluble petroleum sulfonates | 6% |
| xylene | 59% |

The ingredients are combined and ground together in a sand mill to produce particles essentially all of which are smaller than 5 microns. The product can be used directly, extended with oils, or emulsified in water.

UTILITY

The compounds of Formula I are useful as herbicides. They may be applied either pre- or postemergence for the control of undesired vegetation in noncrop areas. By properly selecting rate and time of application, compounds of this invention may be used to modify plant growth beneficially.

The precise amount of the compound of Formula I to be used in any given situation will vary according to the particular end result desired, the use involved, the weeds to be controlled, the soil type, the formulation and mode of application, weather conditions, etc. Since so many variables play a role, it is not possible to state a rate of application suitable for all situations. Broadly speaking, the compounds of this invention are used at levels of about 0.05 to 20 kg/ha with a preferred range of 0.2 to 10 kg/ha. The lower rates of the range will generally be selected for lighter soils, or situations in which maximum persistence is not necessary.

The compounds of Formula I may be combined with other herbicides and are particularly useful in combination with 3-(3,4-dichlorophenyl)-1,1-dimethylurea, the triazines such as 2,4-bis(isopropylamino)-6-(methylthio)-s-triazine, the uracils such as 5-bromo-3-secbutyl-6-methyluracil, N-(phosphonomethyl)glycine, 3-cyclohexyl-1-methyl-6-dimethylamino-s-triazine-2,4(1H,3H)dione, N,N-dimethyl-2,2-diphenylacetamide, 2,4-dichlorophenoxyacetic acid (and closely related compounds), 3-(3,4-dichlorophenyl)-1-methoxy-1-methylurea, 1,1'-dimethyl-4,4'-bipyridinium ion, and monosodium methanearsonate.

The activity of these compounds was discovered in greenhouse tests. The tests are described below and the data resulting from them are shown below.

TEST 1

Seeds of crabgrass (Digitaria sp.), barnyardgrass (Echinochloa crusgalli), wild oats (Avena fatua), Cassia tora, morningglory (Ipomoea sp.), cocklebur (Xanthium sp.), sorghum, corn, soybean, rice, wheat and nutsedge tubers were planted in a growth medium and treated preemergence with the chemicals dissolved in a nonphytotoxic solvent. At the same time, cotton having five leaves (including cotyledonary ones), bush beans with the third trifoliolate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for 16 days, then all species were compared to controls and visually rated for response to treatment.

Ratings for compounds tested by this procedure are recorded in Table 8. The rating system used was based on a scale extending from 0, no effect, to 10, maximum effect. The accompanying letter symbols have the following meanings:

B=burn
C=chlorisis or necrosis
D=defoliation
E=emergence inhibition
G=growth retardation
H=formative effect
L=lodging
P=terminal bud kill
S=albinism
U=unusual pigmentation
6Y=abscised buds or flowers

TABLE 8

| kg/ha | 2-CH₃-C₆H₄-SO₂NHC(O)NH-(4,6-diOCH₃-pyrimidin-2-yl) — 2 | 2-Cl-C₆H₄-SO₂NHC(O)NH-(4,6-diOCH₃-pyrimidin-2-yl) — 2 | C₆H₅-SO₂NHC(O)NH-(4,6-diCH₃-pyrimidin-2-yl) — 2 |
|---|---|---|---|
| POST EMERGENCE | | | |
| BUSH BEAN | | | 1B |
| COTTON | 5C 5D 9G | 9C | 1B |
| MORNING GLORY | 6C 9G | 6C 9G | 2B |
| COCKLEBUR | 2C 9G | 9C | 0 |
| CASSIA | 5C 9G | 9C | 0 |
| NUTSEDGE | 2C 9G | 9C | 0 |
| CRABGRASS | 4G | 3G | 3H |
| BARNYARD GRASS | 3C 9H | 5C 8G | 1B |
| WILD OATS | 2C 8G | 3G | 0 |
| WHEAT | 6G | 1C 6G | 0 |
| CORN | 3C 9G | 5U 9G | 2H |
| SOYBEAN | 2C 9G | 3C 4G | 1B |
| RICE | 2C 9G | 10P 8G | 0 |
| SORGHUM | 7G 5L | 3U 8G | 0 |
| PRE EMERGENCE | | | |
| MORNING GLORY | 10E | 9H | 0 |
| COCKLEBUR | 9G | 8H | 0 |
| CASSIA | 9C | 10E | 0 |
| NUTSEDGE | 10E | 10E | 0 |
| CRABGRASS | 0 | 8G | 0 |
| BARNYARD GRASS | 2H 8G | 9G | 0 |
| WILD OATS | 7G | 8G | 0 |
| WHEAT | 7G | 10E | 0 |
| CORN | 9G | 9H | 0 |
| SOYBEAN | 9G | 10E | 0 |
| RICE | 10E | 9H | 0 |
| SORGHUM | 7G | | 0 |

| kg/ha | C₆H₅-SO₂NHC(O)NH-(4,6-diOCH₃-pyrimidin-2-yl) — 2 | 2-Cl-C₆H₄-SO₂NHC(O)NH-(4,6-diCH₃-pyrimidin-2-yl) — 2 | 2-thienyl-SO₂NHC(O)NH-(4,6-diOCH₃-pyrimidin-2-yl) — 2 |
|---|---|---|---|
| POST EMERGENCE | | | |
| BUSH BEAN | 1C 8G 6Y | 3H 6Y | 3C 9G 6Y |
| COTTON | 4C 7G | 2C 2H | 4C 9G |
| MORNING GLORY | 6G | 3C | 10C |
| COCKLEBUR | 5G | 3C | 5C 9G |

TABLE 8-continued

| | Structure 1: SO₂—NH—C(O)—NH— pyrimidine (OCH₃, CH₃), phenyl-CH₃ | Structure 2: SO₂—NH—C(O)—NH— pyrimidine (CH₃, OCH₃), phenyl-CH₃ | Structure 3: SO₂—NH—C(O)—NH— pyrimidine (CH₃, OCH₃), phenyl-Cl |
|---|---|---|---|
| | 2 | 2 | 2 |
| CASSIA | 2G | 1C | 1C 8G |
| NUTSEDGE | 1C 7G | 0 | 9G |
| CRABGRASS | 2H | 5H | 2G |
| BARNYARD GRASS | 1H | 3H | 1C 5G |
| WILD OATS | 0 | 0 | 1C |
| WHEAT | 2G | 0 | 2G |
| CORN | 1C 6G | 0 | 9H |
| SOYBEAN | 1C 3G | 4G | 3H 9G |
| RICE | 7G | 0 | 5C 9G |
| SORGHUM | 1H 7G | 0 | 5G 5L |
| PRE EMERGENCE | | | |
| MORNING GLORY | 9G | 0 | 9G |
| COCKLEBUR | 1H 9G | 0 | 9G |
| CASSIA | 6G | 10E | 9G |
| NUTSEDGE | 8G | 0 | 10E |
| CRABGRASS | 2C | 5H | 1C |
| BARNYARD GRASS | 1C | 1H | 3S 8G |
| WILD OATS | 5G | 0 | 7G |
| WHEAT | 3G | 5G | 3G |
| CORN | 2H 7G | 2G | 2H 9G |
| SOYBEAN | 8G | 1H | 9G |
| RICE | 10E | 0 | 10E |
| SORGHUM | 2C | 0 | 4G |

| kg/ha | 2 | 2 | 2 |
|---|---|---|---|
| POST EMERGENCE | | | |
| BUSH BEAN | 2C 8G 6Y | 0 | 0 |
| COTTON | 4C 8G | 2H | 1B |
| MORNING GLORY | 9C | 2G | 0 |
| COCKLEBUR | 3C | 0 | 0 |
| CASSIA | 8G 4C | 0 | 0 |
| NUTSEDGE | 1C 5G | 5G | 1C 3G |
| CRABGRASS | 0 | 0 | 0 |
| BARNYARD GRASS | 4C | 0 | 0 |
| WILD OATS | 0 | 2G | 3G |
| WHEAT | 0 | 2G | 2G |
| CORN | 2G | 3G | 0 |
| SOYBEAN | 1C 6G | 2G | 0 |
| RICE | 4G | 2G | 0 |
| SORGHUM | 2G | 0 | 0 |
| PRE EMERGENCE | | | |
| MORNING GLORY | 9G | 10E | 3C |
| COCKLEBUR | — | 7G | 2C |
| CASSIA | 8G | 1C | 3C |
| NUTSEDGE | 8G | 1C 9G | 2C 7G |

TABLE 8-continued

| | | | | | | | POST EMERGENCE | | | | | |
|---|---|---|---|---|---|---|---|---|---|---|---|---|
| CRABGRASS | | | | | | | | | | | | 0 |
| BARNYARD GRASS | | | | | | | | | | | | 4G |
| WILD OATS | | | | | | | | | | | | 6G |
| WHEAT | | | | | | | | | | | | 4G |
| CORN | | | | | | | | | | | | 2C 7G |
| SOYBEAN | | | | | | | | | | | | 3G |
| RICE | | | | | | | | | | | | 9H |
| SORGHUM | | | | | | | | | | | | 7G |

| COMPOUND | | BUSH BEANS | COT-TON | SOR-GHUM | CORN | SOY-BEAN | WHEAT | WILD OATS | RICE | BARN-YARD GRASS | CRAB-GRASS | MORN-ING GLORY | COCKLE-BUR | CAS-SIA | NUT-SEDGE |
|---|---|---|---|---|---|---|---|---|---|---|---|---|---|---|---|
| [structure: NO2-phenyl-SO2NH-C(O)-NH-pyrimidine(OCH3,OCH3)] | 2 | 9C | 9C | 5C 8C 3C 8G | 10C | 9C | 9C | 9C | 9C | 10C | 9C | 9C | 9C | 10C | 10C |
| | 0.4 | 9C | 9C | | 9C | 9C | 3C 7G | 9C | 9C | 10C | 9C | 10C | 9C | 9C | 10C |
| [structure: NO2-phenyl-SO2NH-C(O)-NH-pyrimidine(OCH3,Cl)] | 2 | 9C | 9C | 9C 5C 9G | 9U 9G 5U 9G | 9C | 9C | 9C | 9C | 9C | 9C | 10C | 10C | 9C | 10C |
| | 0.4 | 8C | 8C | | | | 2C 7G | 2C 7G | | | | 10C | 9C | 9C | 10C |
| [structure: NO2-phenyl-SO2NH-C(O)-NH-pyrimidine(Cl,Cl)] | 2 | 5B 5G 2B 3G | 5B 3G 7G 1B 5G | 3B 7G 1B 5G | 3B 8U 1B 2H | 2B 6H 1B | 3B 1B | 3B 5G 1B | 3B 5G 1B 8G | 5B 9G 3B 7H | 4C 8G 5C 9G | 5B 9G 9C | 10C 9C | 7C 1B | 9C 7G |
| | 0.4 | 9C 3S 6G 6Y | | | | | | 2C 7G | | | | | | | |

| | | | | | | | PRE-EMERGENCE | | | | | |
|---|---|---|---|---|---|---|---|---|---|---|---|---|
| COMPOUND | SOR-GHUM | CORN | SOY-BEAN | WHEAT | WILD OATS | RICE | BARN-YARD GRASS | CRAB-GRASS | MORN-ING GLORY | COCKLE-BUR | CAS-SIA | NUT-SEDGE |
| [structure: NO2-phenyl-SO2NH-C(O)-NH-pyrimidine(OCH3,OCH3)] | 10H | 9G | 9H | 9G | 9G | 10E | 10H | 9G | 10E | 9H | 9G | 10E |
| | 9H | 9H | 9H | 8G | 8G | 10E | 9H | 9H | 10E | 9H | 9G | 10E |

TABLE 8-continued (Table contains two chemical structures with accompanying test data at rates 2 and 0.4; values include entries such as 9H, 9G, 10E, 9C, 8G, 8H, 7G, 5H, 2H, 4G, 6G, 3G, 1C, 2C, 5C, and combined multi-line entries. Detailed column alignment not reliably discernible from the image.)

TEST II

Two 25 cm diameter plastic bulb pans were filled with fertilized and limed Fallsington silt loam soil. One pan was planted with corn, sorghum and several grassy weeds. The other pan was planted with soybeans, purple nutsedge (*Cyperus rotundus*), and several broadleaf weeds. The following grassy and broadleaf species were planted: crabgrass (*Digitaria sanguinalis*), barnyardgrass (*Echinochloa crusgalli*), wild oats (*Avena fatua*), johnsongrass (*Sorghum halepense*), giant foxtail (*Setaria faberii*), Kentucky bluegrass (*Poa pratensis*), cheatgrass (*Bromus secalinus*), mustard (*Brassica arvensis*), cocklebur (*Xanthium pennsylvanicum*), pigweed (*Amaranthus retroflexus*), curly indigo (*Aeschynomene virginica*), morningglory (*Ipomoea hederacea*), cassia (*Cassia tora*), teaweed (*Sida spinosa*), velvetleaf (*Abutilon theophrasti*), and jimsonweed (*Datura stramonium*). In addition, two 12.5 cm diameter paper cups were filled with prepared soil; one was planted with rice and wheat, the other with sugarbeets. The above four containers were treated preemergence, i.e., the compounds were sprayed on the soil surface before seed germination.

Twenty-eight days after treatment, the plants were visually rated for injury symptoms utilizing the rating system as described for Test I. The test results are summarized in Table 9.

TABLE 9
FALLSINGTON SANDY LOAM

| | 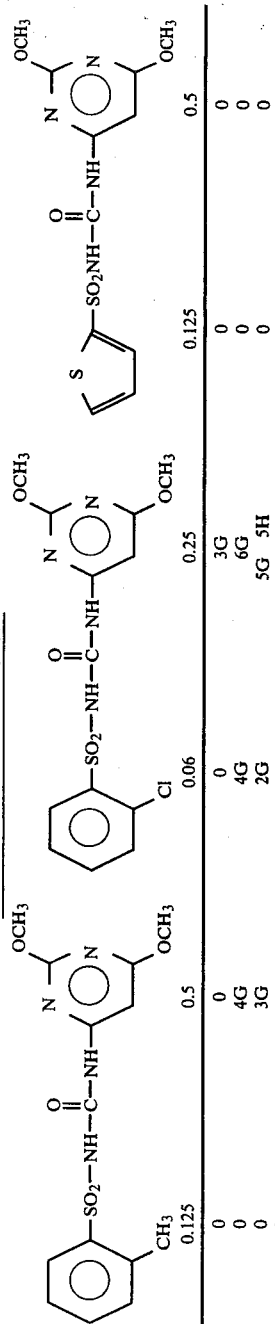 | 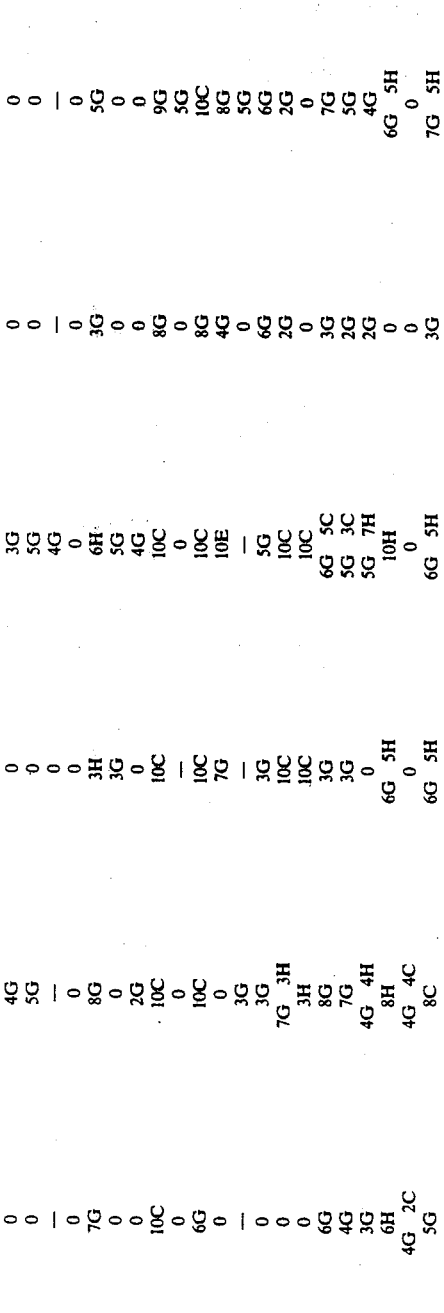 | 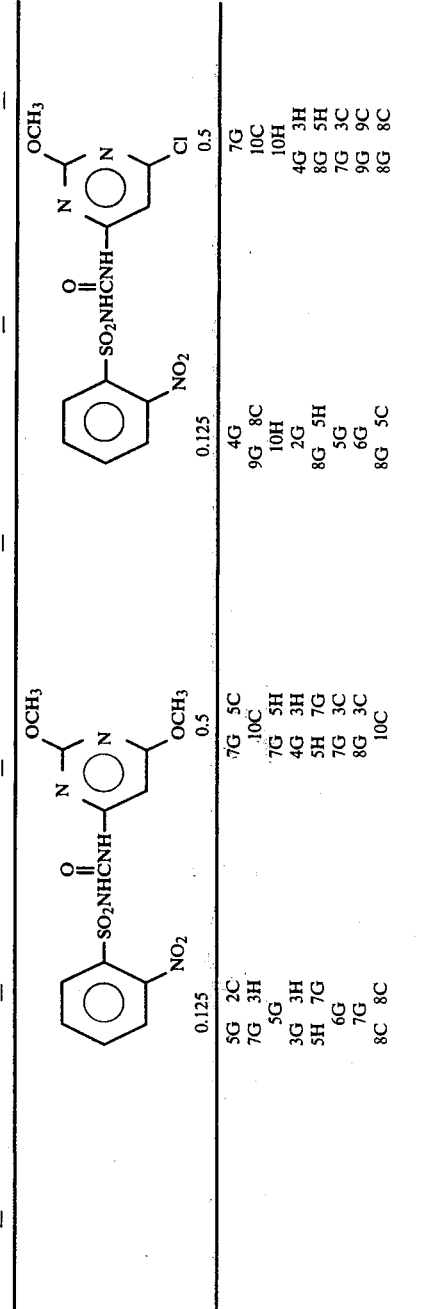 |  |
|---|---|---|---|---|
| Rate kg/ha | 0.125 | 0.5 | 0.06 | 0.25 | 0.125 | 0.5 |
| CRABGRASS | 0 | 0 | 0 | 3G | | |
| BARNYARDGRASS | 0 | 4G | 4G | 6G | | |
| SORGHUM | 0 | 3G | 2G | 5G 5H | | |
| WILD OATS | 0 | 4G | 0 | 3G | | |
| JOHNSONGRASS | 0 | 5G | 0 | 5G | | |
| DALLISGRASS | — | — | 0 | 4G | | |
| GIANT FOXTAIL | 0 | 0 | 0 | 0 | | |
| KY. BLUEGRASS | 7G | 8G | 3H | 6H | | |
| CHEATGRASS | 0 | 0 | 3G | 5G | | |
| CORN | 0 | 2G | 0 | 4G | | |
| MUSTARD | 10C | 10C | 10C | 10C | | |
| COCKLEBUR | 0 | 0 | — | 0 | | |
| PIGWEED | 6G | 10C | 10C | 10C | | |
| NUTSEDGE | 0 | 0 | 7G | 10E | | |
| H. INDIGO | — | — | — | — | | |
| MORNINGGLORY | 0 | 3G | 3G | 5G | | |
| CASSIA | 0 | 3G | 10C | 10C | | |
| TEAWEED | 0 | 3H | 10C | 10C | | |
| VELVETLEAF | 6G | 8G | 3G | 6G 5C | | |
| JIMSONWEED | 4G | 7G | 3G | 5G 3C | | |
| SOYBEAN | 3G | 4G 4H | 0 | 5G 7H | | |
| RICE | 6H | 8H | 6G 5H | 10H | | |
| WHEAT | 4G 2C | 4G 4C | 0 | 0 | | |
| SUGARBEETS | 5G | 8C | 6G 5H | 6G 5H | | |
| Cotton | — | — | — | — | | |

| | 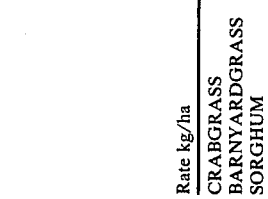 | 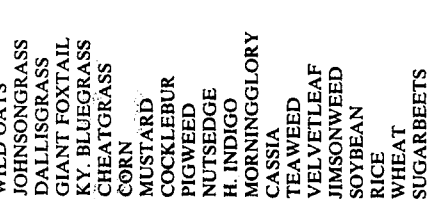 | 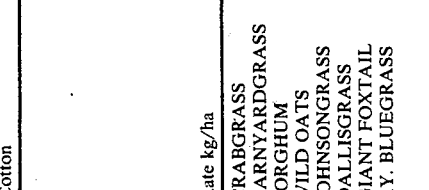 |  |
|---|---|---|---|---|
| Rate kg/ha | 0.125 | 0.5 | 0.125 | 0.5 |
| CRABGRASS | 5G 2C | 7G 5C | 4G | 7G |
| BARNYARDGRASS | 7G 3H | 10C | 9G 8C | 10C |
| SORGHUM | 5G | 7G 5H | 10H | 10H |
| WILD OATS | 3G 3H | 4G 3H | 2G | 4G 3H |
| JOHNSONGRASS | 5H 7G | 5H 7G | 8G 5H | 8G 5H |
| DALLISGRASS | | 7G 3C | 5G | 7G 3C |
| GIANT FOXTAIL | 6G | 8G 3C | 6G | 9G 9C |
| KY. BLUEGRASS | 8C 8C | 10C | 8G 5C | 8G 8C |

TABLE 9-continued

| | FALLSINGTON SANDY LOAM | | | | | |
|---|---|---|---|---|---|---|
| CHEATGRASS | 7G | | 8G | 5C | 7G | | 8G | |
| CORN | 2G | | 6G | 5H | 7G | | 9C | 9G |
| MUSTARD | 10C | | 10C | | 10C | | 10C | |
| COCKLEBUR | 7G | 3C | 7G | 5C | 7G | 5C | 7G | 5C |
| PIGWEED | 8G | 5C | 10C | | 10E | | 10E | |
| NUTSEDGE | 10E | | 10E | | 10E | | 10E | |
| H. INDIGO | — | | — | | — | | — | |
| MORNINGGLORY | 8G | | 8G | | 8G | | 9G | |
| CASSIA | 8G | | 7G | | 7G | | 3C | 8G |
| TEAWEED | 8G | 5C | 8G | 7C | 8G | 7C | 8G | 8C |
| VELVETLEAF | 8G | 5C | 8G | 5C | 8G | 5C | 8G | 8C |
| JIMSONWEED | 5G | | 6G | | 6G | 5C | 6G | 2C |
| SOYBEAN | 8G | 5H | 9G | 9H | 7G | 5H | 8G | 5H |
| RICE | 6G | 5C | 10C | | 10C | | 10C | |
| WHEAT | 0 | | 4G | | 0 | | 3G | |
| SUGARBEETS | 9G | 9C | 9G | 9C | 10C | | 10C | |
| Cotton | 8G | | 8G | | 8G | | 9G | |

Test III

Twenty-five cm-diameter plastic pots filled with Fallsington silt loam were planted with soybean, cotton, alfalfa, corn, rice, wheat, sorghum, velvetleaf (*Abutilon theophrasti*), sesbania (*Sesbania exaltata*), cassia (*Cassia tora*), morningglory (Ipomoea sp.), jimsonweed (*Datura stramonium*), cocklebur (Xanthium pennsylvanicum), crabgrass (Digitaria sp.), nutsedge (*Cyperus rotundus*), barnyardgrass (*Echinochloa crusgalli*), giant foxtail (*Setaria faberii*), and wild oats (*Avena fatua*). Approximately 2½ weeks after planting, the young plants and the soil around them were sprayed overall with the test chemicals dissolved in a nonphytotoxic solvent. Fourteen days after treatment, all species were compared to untreated controls and visually rated for response to treatment utilizing the rating system as described in Test I. The results are summarized in Table 10.

according to species to achieve desirable effects with a minimum of phytotoxicity. Both vegetative and reproductive growth may be controlled. Previous examples and the one given below illustrate the activity of the compounds of this invention as growth regulants. In sugarcane and sorghum, a "chemical ripening" effect may be produced which results in a greater yield of soluble solids (mostly sugars). In many other grasses, growth and seed stalk development are restricted by these compounds, thereby reducing mowing requirements. These compounds are also useful for growth control of woody and herbaceous broadleaf plants.

Test Description

The compounds in the table below were applied to tendercrop beans ("bush" type). The compounds were applied in a suitable nonphytotoxic solvent when the developing tendercrop beans were in the early flower-bud stage. Treated plants and untreated controls were

TABLE 10

Over-the-Top Soil/Foliage Treatment

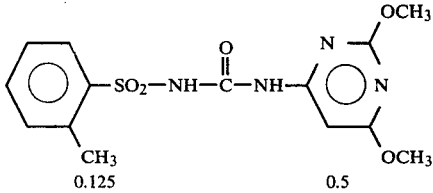    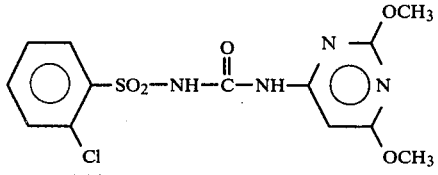

| Rate kg/ha | 0.125 | 0.5 | 0.06 | 0.25 |
|---|---|---|---|---|
| Soybean | 10G 5C | 10G 6C | 10G 9C | 10C |
| Velvetleaf | 10G 7C | 10G 9C | — | 10C |
| Sesbania | 10G 9C | 10G 6C | 10C | 10C |
| Cassia | 5G 3C | 10G 6C | 10C | 10C |
| Cotton | 5G 2C | 8G 3C | 10G 9C | 10G 6C |
| Morningglory | 5G 2C | 10G 4C | 10G 3C | 10C |
| Alfalfa | 5G 2C | 10G 4C | 6G | 6G |
| Jimsonweed | 5G 2C | 10G 3C | 7G 3C | 10G 5C |
| Cocklebur | 100 | — | 3G | 10G 8C |
| Corn | 5G 3H | 10G 3C | 7G | 7G |
| Crabgrass | 0 | 2G | 4G | 6G |
| Rice | 5G | 5G | 0 | 5G 2C |
| Nutsedge | 10G 3C | 10G 4C | 2C | 10G 6C |
| Barnyardgrass | 5G | 10G 3C | 7G | 8G |
| Wheat | 3G | 5G | 4G | 5G |
| Giant Foxtail | 0 | 6G | 0 | 4G |
| Wild Oats | 0 | 5G | 3G | 4G |
| Sorghum | 3G | 6G | 3G | 4G 3C |
| Yellow Rocket | | | | |
| Pigweed | | | | |
| Johnsongrass | | | | |

PLANT GROWTH REGULANT USES

In addition to their use as herbicides, compounds of Formula I are also useful as agents to beneficially modify growth of selected plant species. Rates (usually 0.01 to 1.0 kg/ha) and timing of application are selected maintained in a greenhouse and response ratings taken 1 and 4 weeks after treatment. Pod yields were taken between 3 and 4 weeks after treatment. Yield results (number and weight) are recorded as a percentage of untreated controls. The test results are summarized in Table 11.

TABLE 11

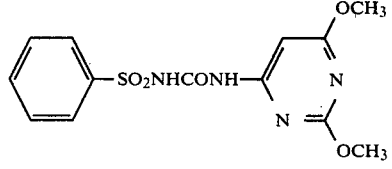    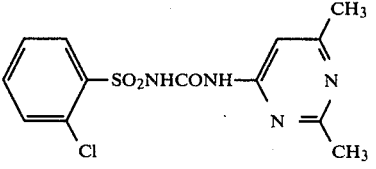

| Rate kg/hectare | 0.5 | 2.0 |
|---|---|---|
| Plant Response: | | |
| 1 week | 1C | 0 |
| 3 weeks | 2G | 2G, 2C |
| Pod Yield | 90% | 100% |
| Weight of | | |

TABLE 11-continued

| Fruit | 40% | 70% | |
|---|---|---|---|

Structure: thiophene-SO₂NHCONH-pyrimidine with OCH₃ groups at 4 and 6 positions

| Rate kg/hectare | 0.25 | 0.06 | 0.015 |
|---|---|---|---|
| Plant Response: | | | |
| 1 week | 9G, 2S | 5G, 2H | 2G |
| 3 weeks | 5G, 3H | 3G, 1C | 0 |
| Pod Yield | 80% | 60% | 100% |
| Weight of Fruit | 50% | 60% | 80% |

What is claimed is:

1. A compound having the formula:

$$R_1-SO_2-NH-\overset{W}{\underset{\|}{C}}-NH-\underset{N=\underset{Y}{\diagdown}}{\overset{X}{\diagup}}\hspace{-4pt}\bigcirc\hspace{-4pt}N$$

wherein
R₁ is

[phenyl ring with R₂, R₃, H substituents]

R₂ is nitro, trifluoromethyl, chlorine or methyl;
R₃ is hydrogen;
W is independently oxygen or sulfur; and
X and Y are methoxy or an agriculturally suitable salt thereof.

2. A compound of claim 1 wherein R₂ is chlorine, nitro or methyl and R₃ is hydrogen.

3. A compound of claim 1 wherein R₂ is chlorine, nitro or methyl; R₃ is hydrogen; and W is oxygen.

4. A compound of claim 3 which is N-[(2,6-dimethoxypyrimidin-4-yl)aminocarbonyl]-2-methylbenzenesulfonamide.

5. A compound of claim 3 which is N-[(2,6-dimethoxypyrimidin-4-yl)aminocarbonyl]-2-chlorobenzenesulfonamide.

6. A compound of claim 3 which is N-[(2,6-dimethoxypyrimidin-4-yl)aminocarbonyl]-2-nitrobenzenesulfonamide.

7. A compound of claim 3 which is N-[(2-methoxy-6-chloropyrimidin-4-yl)aminocarbonyl]-2-nitrobenzenesulfonamide.

8. A compound of claim 3 which is N-[(2,6-dichloropyrimidin-4-yl)aminocarbonyl]-2-nitrobenzenesulfonamide.

9. A composition suitable for controlling the growth of undesired vegetation which comprises an effective amount of a compound of claim 1 and at least one of the following: surfactant, solid or liquid diluent.

10. A composition suitable for controlling the growth of undesired vegetation which comprises an effective amount of a compound of claim 2 and at least one of the following: surfactant, solid or liquid diluent.

11. A composition suitable for controlling the growth of undesired vegetation which comprises an effective amount of a compound of claim 3 and at least one of the following: surfactant, solid or liquid diluent.

12. A composition suitable for controlling the growth of undesired vegetation which comprises an effective amount of the compound of claim 4 and at least one of the following: surfactant, solid or liquid diluent.

13. A composition suitable for controlling the growth of undesired vegetation which comprises an effective amount of the compound of claim 5 and at least one of the following: surfactant, solid or liquid diluent.

14. A composition suitable for controlling the growth of undesired vegetation which comprises an effective amount of the compound of claim 6 and at least one of the following: surfactant, solid or liquid diluent.

15. A composition suitable for controlling the growth of undesired vegetation which comprises an effective amount of the compound of claim 7 and at least one of the following: surfactant, solid or liquid diluent.

16. A composition suitable for controlling the growth of undesired vegetation which comprises an effective amount of the compound of claim 8 and at least one of the following: surfactant, solid or liquid diluent.

17. A method for controlling the growth of undesired vegetation which comprises applying to the locus of the undesired vegetation an effective amount of a compound of claim 1.

18. A method for controlling the growth of undesired vegetation which comprises applying to the locus of the undesired vegetation an effective amount of a compound of claim 1.

19. A method for controlling the growth of undesired vegetation which comprises applying to the locus of the undesired vegetation an effective amount of a compound of claim 1.

20. A method for controlling the growth of undesired vegetation which comprises applying to the locus of the undesired vegetation an effective amount of a compound of claim 1.

21. A method for controlling the growth of undesired vegetation which comprises applying to the locus of the undesired vegetation an effective amount of a compound of claim 2.

22. A method for controlling the growth of undesired vegetation which comprises applying to the locus of the undesired vegetation an effective amount of a compound of claim 3.

23. A method for controlling the growth of undesired vegetation which comprises applying to the locus of the undesired vegetation an effective amount of the compound of claim 4.

24. A method for controlling the growth of undesired vegetation which comprises applying to the locus of the undesired vegetation an effective amount of the compound of claim 5.

25. A method for controlling the growth of undesired vegetation which comprises applying to the locus of the undesired vegetation an effective amount of the compound of claim 6.

26. A method for controlling the growth of undesired vegetation which comprises applying to the locus of the undesired vegetation an effective amount of the compound of claim 7.

27. A method for controlling the growth of undesired vegetation which comprises applying to the locus of the undesired vegetation an effective amount of the compound of claim 8.

28. A method for regulating the growth of vegetation which comprises applying to the locus of the vegetation an effective amount of a compound of claim 1.

29. A method for regulating the growth of vegetation which comprises applying to the locus of the vegetation an effective amount of a compound of claim 1.

30. A method for regulating the growth of vegetation which comprises applying to the locus of the vegetation an effective amount of a compound of claim 1.

31. A method for regulating the growth of vegetation which comprises applying to the locus of the vegetation an effective amount of a compound of claim 1.

32. A method for regulating the growth of vegetation which comprises applying to the locus of the vegetation an effective amount of a compound of claim 2.

33. A method for regulating the growth of vegetation which comprises applying to the locus of the vegetation an effective amount of a compound of claim 3.

34. A composition suitable for use as a growth regulant which comprises an effective amount of a compound of claim 1 and at least one of the following: surfactant, solid or liquid diluent.

35. A composition suitable for use as a growth regulant which comprises an effective amount of a compound of claim 2 and at least one of the following: surfactant, solid or liquid diluent.

36. A composition suitable for use as a growth regulant which comprises an effective amount of a compound of claim 3 and at least one of the following: surfactant, solid or liquid diluent.

* * * * *